(12) United States Patent
Houfburg

(10) Patent No.: US 6,283,966 B1
(45) Date of Patent: Sep. 4, 2001

(54) SPINAL SURGERY TOOLS AND POSITIONING METHOD

(75) Inventor: Rodney L. Houfburg, Prior Lake, MN (US)

(73) Assignee: Sulzer Spine-Tech Inc., Minneapolis, MN (US)

( * ) Notice: Subject to any disclaimer, the term of this patent is extended or adjusted under 35 U.S.C. 154(b) by 0 days.

(21) Appl. No.: 09/348,894

(22) Filed: Jul. 7, 1999

(51) Int. Cl.[7] .................................................. A61B 17/56
(52) U.S. Cl. ................. 606/61; 606/90; 606/96; 623/17.11
(58) Field of Search ................. 606/61, 60, 90, 606/99, 100, 96, 104; 623/17.11; 128/898

(56) References Cited

U.S. PATENT DOCUMENTS

| | | |
|---|---|---|
| 4,501,269 | 2/1985 | Bagby . |
| 4,834,757 * | 5/1989 | Brantigan .......................... 623/17.11 |
| 4,877,020 | 10/1989 | Vich . |
| 4,878,915 | 11/1989 | Brantigan . |
| 4,961,740 | 10/1990 | Ray et al. . |
| 5,015,247 | 5/1991 | Michelson . |
| 5,015,255 | 5/1991 | Kuslich . |
| 5,026,373 | 6/1991 | Ray et al. . |
| 5,055,104 | 10/1991 | Ray . |
| 5,425,772 | 6/1995 | Brantigan . |
| 5,443,514 | 8/1995 | Steffee . |
| 5,484,437 | 1/1996 | Michelson . |
| 5,489,307 * | 2/1996 | Kuslich et al. ................... 623/17.11 |
| 5,489,308 | 2/1996 | Kuslich et al. . |
| 5,571,109 | 11/1996 | Bertagnoli . |
| 5,609,636 | 3/1997 | Kohrs et al. . |
| 5,669,909 | 9/1997 | Zdeblick et al. . |
| 5,741,253 | 4/1998 | Michelson . |
| 5,782,919 * | 7/1998 | Zdeblick et al. ................. 623/17.11 |
| 5,797,909 | 8/1998 | Michelson . |
| 5,865,847 * | 2/1999 | Kohrs et al. ...................... 623/17.11 |
| 6,059,790 * | 5/2000 | Sand et al. ............................. 606/61 |
| 6,086,595 * | 7/2000 | Yonemura et al. .................... 606/99 |
| B1 4,961,740 | 1/1997 | Ray et al. . |

* cited by examiner

Primary Examiner—Pedro Philogene
(74) Attorney, Agent, or Firm—Merchant & Gould P.C.

(57) ABSTRACT

Instruments and methods are disclosed for positioning a spinal implant within an intervertebral disc space between adjacent vertebrae. The invention advantageously provides for positioning of the implant at a predetermined location with reduced likelihood of implant positioning which deviates from the predetermined location.

23 Claims, 10 Drawing Sheets

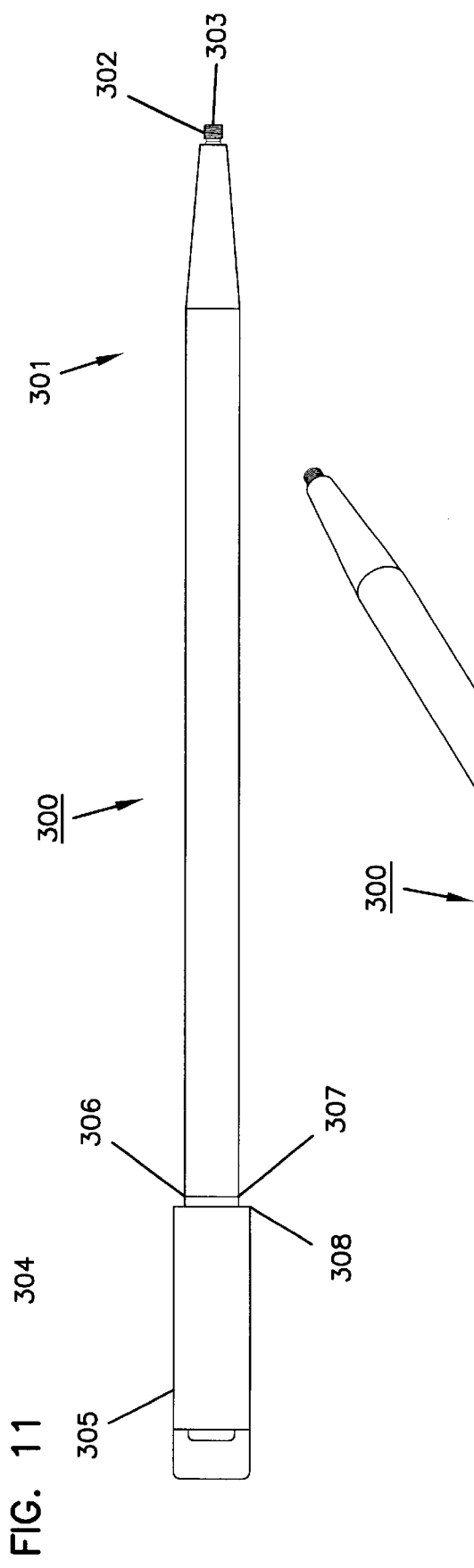

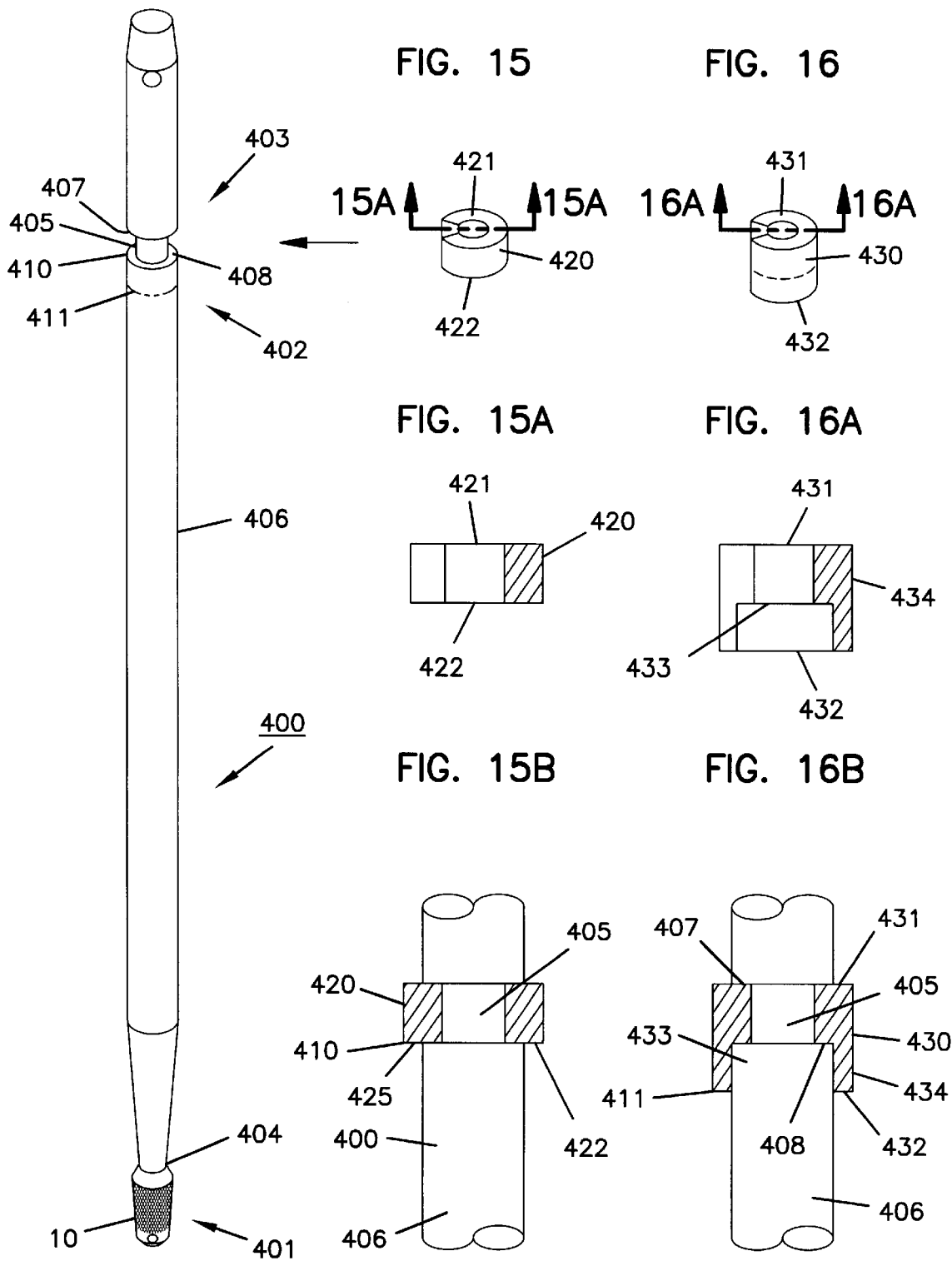

SPINAL SURGERY TOOLS AND POSITIONING METHOD

FIELD OF THE INVENTION

This invention pertains to intervertebral fusion. Specifically, the invention is directed to instrumentation and methods for insertion of spinal implants between opposing vertebral bodies.

BACKGROUND OF THE INVENTION

Chronic back problems can cause pain and disability for a large segment of the population. Frequently, the cause of back pain is traceable to diseased disc material between opposing vertebrae. When the disc material is diseased, the opposing vertebrae may be inadequately supported, resulting in persistent pain.

Surgical techniques have been developed to remove the diseased disc material and fuse the joint between opposing vertebral bodies. Arthrodesis or fusion of the intervertebral joint can reduce the pain associated with movement of an intervertebral joint having diseased disc material. Generally, fusion techniques involve removal of the diseased disc, distracting the intervertebral joint space, drilling a bore for receiving the implant and inserting the implant between the opposing vertebral bodies.

Spinal fusion implants and related surgical instruments for implanting a fusion device are known and disclosed in, for example, U.S. Pat. Nos. 5,741,253; 5,658,337; 5,609,636; 5,505,732; 5,489,308; 5,489,307; 5,484,437; 5,458,638; 5,055,104; 5,026,373; 5,015,247; 4,961,740 and 4,501,269. The disclosure of each of these patents are incorporated herein by reference. Procedures for fusing an intervertebral joint space typically include placement of at least two cylindrical implants in parallel arrangement between the opposing vertebrae.

Some presently available systems for intervertebral fusion provide for preparing an implant site through a hollow tube. Procedures for preparing an implant site through a hollow tube are shown in, for example, U.S. Pat. Nos. 5,484,437; 5,489,307 and 5,505,732. The disclosure of each of these patents are incorporated herein by reference. In some procedures, the implants are also inserted into the prepared site through the hollow tube. Preparing the implant site by passing instruments through a hollow tube advantageously provides for an isolated surgical field with reduced chance of injury to soft tissues surrounding the surgical site.

Often times, the degenerative changes of the diseased disc cause a collapse of the intervertebral disc space. Thus, prior to implantation, the intervertebral disc space may be distracted to restore the normal height of the disc space or the normal relationship between the vertebrae to be fused. Maintaining the restored disc space height and/or vertebral relationships throughout preparation of the implant site is important for the ultimate stability at the fusion site. This may be particularly true when a lordotic implant is used to restore or establish a particular degree of lordosis between adjacent vertebrae.

However, most presently available implant procedures do not take into account events which can cause deviation of the final implant position from the position selected by the surgeon during initial implant site determination. Deviation of the final implant position from the initially selected position can result in, for example, reduced fusion site stability, implant migration, implant loosening, implant subsidence and improper purchase of an anchoring arrangement of an implant (e.g., threads, spikes, ridges, knurls, etc.), at the fusion site. In the case of a lordotic implant, deviation of the final implant position can also cause deviation from the desired degree of lordosis, deviation in the amount of distraction (i.e., disc space height), and/or deviation in the amount of purchase of the implant anchoring arrangement into the surrounding cortical bone.

Thus, while present procedures for implantation through a hollow tube help to reduce the chance of iatrogenic tissue trauma caused by the implant procedure, the overall results of the implant may be not be optimal due to a deviation of the final placement of the implant from the desired placement position.

Accordingly, there is a need for instrumentation and methods which insure that the final position of a spinal implant is in the position which was initially established by the surgeon during distraction of the intervertebral joint space. The present invention is directed to this need.

SUMMARY OF THE INVENTION

Throughout the specification, guidance may be provided through lists of examples. In each instance, the recited list serves only as a representative group. It is not meant, however, that the list is exclusive.

The present invention is directed to instruments and methods for increased precision of placement of a spinal fusion implant in the intervertebral disc space. The principles and methods disclosed are suitable for implantation of all types of implants including, for example, threaded implants, non-threaded implants, cylindrical implants, non-cylindrical implants, lordotic implants, expandable implants, etc., through an anterior, posterior or lateral approach.

In one embodiment, a method according to the invention includes a step of determining a desired position of the spinal implant within an intervertebral disc space between adjacent first and second vertebral bodies and using the desired position as a first reference point. The first reference point is then correlated with a second reference point located exterior to the intervertebral space. The second reference point provides a limit to the advancement of the instruments used to prepare an implant bore. In some embodiments, a third reference point may also be used.

In one embodiment, the first reference point can be established based on the position of a distraction device, such as a distraction plug. Alternatively, an object other than a distraction device and/or a diagnostic image can be used to establish a first reference point.

The invention also provides instruments and kits which are advantageous for use according to the invention.

BRIEF DESCRIPTION OF THE DRAWINGS

FIG. 11 is a side view of one embodiment of an obturator and obturator cap;

FIG. 12 is perspective view of the obturator and obturator cap illustrated in FIG. 11;

FIG. 13 is a perspective view of an alternative embodiment of an obturator cap;

FIG. 14 is a perspective view of an alternative embodiment of an obturator and distraction plug;

FIG. 15 is a perspective view of one embodiment of a stop ring according to the invention;

FIG. 15a is a sectional view through line a—a of the stop ring of FIG. 15;

FIG. 15b is a sectional view (rotated 90° from the view of FIG. 15a) of the stop ring of FIGS. 15 and 15a, positioned on the proximal end of the obturator of FIG. 14;

FIG. 16 is an alternative embodiment of a stop ring according to the invention;

FIG. 16a is a sectional view through line a—a of the stop ring of FIG. 16; and

FIG. 16b is a sectional view (rotated 90° from the view of FIG. 16a) of the stop ring of FIGS. 16 and 16a, positioned on the proximal end of the obturator of FIG. 14.

DETAILED DESCRIPTION OF THE INVENTION

Figure 1:
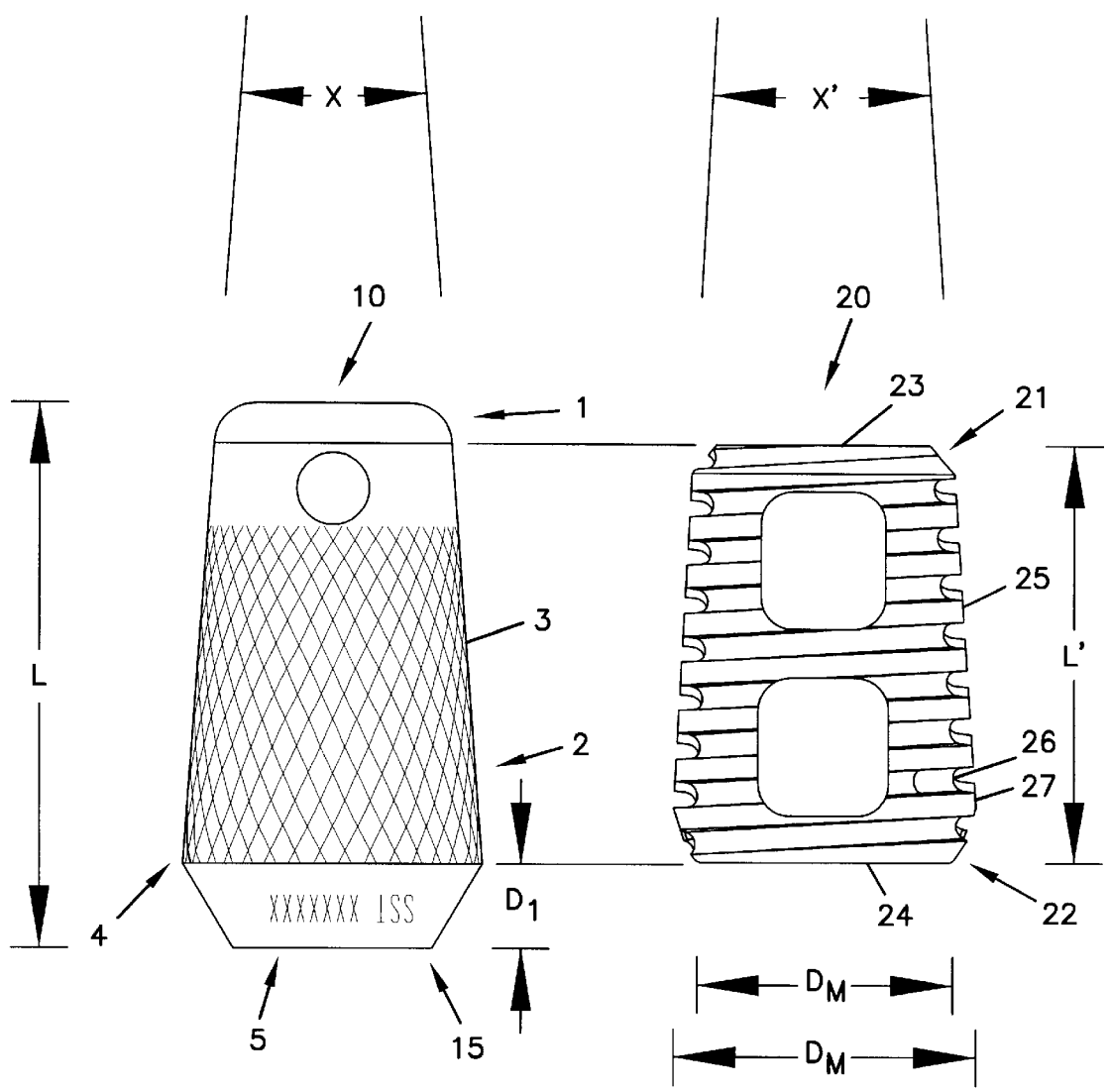
FIG. 1 illustrates a lordotic distraction plug and implant suitable for the present invention.

The present invention is directed to instrumentation and procedures for increased precision of placement of a spinal fusion implant within the intervertebral disc space. The disclosed instrumentation and procedures can be used for installation of most spinal fusion implants from an anterior, lateral or posterior approach. Examples of implants suitable for use according to the invention include threaded implants (e.g., U.S. Pat. Nos. 4,877,020, 5,015,247, 5,489,308), non-threaded implants (e.g., U.S. Pat. Nos. 4,501,269, 4,743,256, 4,834,757, 4,878,915), cylindrical implants (e.g., U.S. Pat. Nos. 4,501,269, 4,961,740, 5,015,247, 5,026,373 and 5,489, 308), non-cylindrical implants (e.g., U.S. Pat. Nos. 4,834, 757, 5,425,772, 5,609,636 and 5,658,337) lordotic implants (e.g., U.S. Pat. Nos. 5,669,909 and 5,865,847), expandable implants, etc. The disclosure of each of the foregoing patents are incorporated herein by reference.

According to the present invention, an "implant site" refers to the location of the implant between adjacent vertebrae. The "implant bore" refers to the bore formed for insertion of the implant between adjacent vertebrae. The implant bore can be threaded or unthreaded depending on the type of implant to be inserted and/or the stage of preparation of the implant bore. Unless otherwise stated, the phrase "selected implant position" refers to the position selected by the physician for placement of the implant within the disc space. The selected implant position provides the surgeon with a reference point for guiding instruments used to prepare the implant bore to ensure final placement of the implant at the selected implant position.

The present invention helps reduce the likelihood of deviation of the final implant position from the position initially selected by the surgeon. Enhancing the likelihood of positioning the implant at the selected implant position facilitates greater coaptation between the implant and the implant bore to provide greater fusion stability, greater motion segment stability, faster fusion, reduced pain, reduced chance of migration, reduced chance of subsidence, etc. In addition, and particularly in the case of a lordotic implant, the precision provided by the present invention increases the consistency between the desired and actual: height of the disc space, degree of lordosis and amount of purchase of the implant into the cortical bone at the end plates.

Thus, the invention provides increased correlation between an initially selected implant location and the final location of the implanted spinal implant. In general, the invention provides for placement of the implant at the selected position by providing and maintaining a substantially invariable reference point for controlling the position of instruments used to prepare the implant bore. One problem with prior systems for spinal implant placement is the variability in the range of movement of the instruments used to prepare the implant bore which is discussed further below.

Throughout the specification, unless stated otherwise, the terms "proximal" and "distal" are relative terms, the term "proximal" referring to a location nearest the surgeon and the term "distal" referring to a location farthest from the surgeon. So, in the case of performing a vertebral fusion from an anterior approach, the anterior surfaces of the vertebrae are "proximal" and the posterior surfaces of the vertebrae are "distal" relative to the surgeon performing the procedure. Likewise, in a posterior approach, the posterior vertebral surfaces are proximal and the anterior surfaces are distal.

Generally, when preparing an implant site using known methods, the instruments used to drill or tap a bore for receiving a threaded implant are advanced into the disc space from a proximal to distal direction. That is, in an anterior approach the instruments are advanced from the anterior surface (proximal) towards the posterior surface (distal) and in a posterior approach the instruments are advanced from the posterior surface (proximal) towards the anterior surface (distal). Similar relative orientations also apply for lateral approaches.

Throughout this application, the invention is described by reference to fusion of two lumbar vertebrae through an anterior approach. However, it will be appreciated that the methods and instruments disclosed can also be used for fusion of vertebrae in other regions of the spinal column through an anterior, posterior or lateral approach.

Typically, prior to preparing the implant bore, the amount of distraction, degree of lordosis (if any), amount of implant purchase and appropriate implant size are estimated from survey diagnostic images using known procedures. In some known methods, a distraction device which provides the appropriate disc space height and degree of lordotic distraction is inserted into the disc space. According to this method, in an anterior approach, the leading face of the distraction device is distally advanced into the disc space until the trailing face is within the anterior margins of the vertebral bodies at a position selected by the surgeon. Once the distraction device is inserted in the disc space, a hollow guide tube is anchored to the vertebral surfaces across the disc space and over the distraction device. In addition to keeping nerves, blood vessels or other tissues out the surgical field of the implant site, the guide tube also guides the lateral position of the instruments used to prepare the site.

Axial guidance of the instruments can be provided by the proximal end of the guide tube acting as an affirmative stop to distal advancement of the instruments. As used herein, "axial guidance" refers to the ability to control the depth of distal advancement of an instrument into the disc space. Thus, improper positioning of the proximal end of the guide tube can result in over drilling or under drilling the implant site relative to the drilling depth necessary to create a bore of an appropriate depth for positioning the implant at the selected implant position.

Often times improper positioning of the proximal end of the guide tube is a direct result of variability which can occur when positioning the distal end of the guide tube against the vertebral surfaces. For example, one cause of variability of the position of the distal end of the guide tube includes irregularities or undulations at the surface of the vertebrae against which the distal end of the tube is placed. In addition, or alternatively, when teeth or other similar arrangement are present for anchoring the distal end of the guide tube to the vertebrae, variability in the depth of penetration of the teeth into the vertebrae directly results in variability in the position of the proximal end of the guide tube.

The present invention overcomes many problems caused by variability in the position of the proximal end of the guide tube by using a reference point for positioning the instruments that is directly related to the selected implant position. Thus, in one embodiment, the invention provides for axially guiding instruments used to prepare the implant site by reference to a first reference point located within the intervertebral disc space to be fused. This reference point may be determined by visually establishing the reference from, for example, a diagnostic image, or from placement of an object, such as a distraction device, Steinman pin, or other apparatus into the disc space, or a combination of such methods. Once the first reference point is determined, a second reference point can be established exterior to the disc space at a fixed distance way from the first reference point. The second reference point can then be used to control the depth of insertion of all instruments used to prepare the implant bore. Controlling the depth of advancement of the instruments used to prepare an implant bore, relative to a reference point directly related to the selected implant position, greatly facilitates placement of the implant at the selected site.

The second reference point can provide axial control to the instruments through a direct or indirect guidance arrangement. A direct guidance arrangement can control the instrument position by, for example, providing a visual indicator for visually indicating when to stop advancement of the instruments. Alternatively, the second reference point can provide indirect guidance of instrument position by providing an indicator for positioning an affirmative stop arrangement, such as the proximal end of a hollow guide tube. Thus, the affirmative stop arrangement acts to limit distal advancement into the disc space before the instruments reach a position which would create an implant site that deviates from the site necessary to position the implant at the selected position.

In an alternative embodiment, the first reference point within the intervertebral space can be used to establish a second reference point at a location exterior to the intervertebral space, for example at the surface of one or both of the vertebrae on either side of the disc space. According to this embodiment, after the second reference point is established, a third reference point can be established at a fixed distance from the second reference point. As described above, the fixed reference point (in this case the third reference point) can be used to directly or indirectly axially guide the instruments used to prepare an implant site.

DETAILED DESCRIPTION OF THE ILLUSTRATED EMBODIMENT

The present invention is particularly advantageous for use in implanting a lordotic implant from an anterior approach. For this reason, one preferred embodiment will be described with illustrations and explanation for implantation of a lordotic implant. It will be appreciated, however, that the instrumentation and procedures described can also be used with non-lordotic implants or implantation instrumentation for implanting the implant through an anterior, posterior or lateral approach.

I. Implantation of a Lordotic Implant Through an Anterior Approach

In the present discussion, a distraction device is used to distract the disc space and establish a first reference point. As used herein, a "distraction device" includes any device which when inserted into the disc space exerts a force against the end plates of the vertebrae adjacent the disc space. In the presently described embodiment, the distraction device is a distraction plug. A distraction plug can be particularly advantageous in some applications. However, it will be appreciated that distraction devices, radiographs or other method or device for defining a first reference point within the intervertebral space can be used within the scope and principles of the present invention. Distraction plugs, implants and instruments suitable for implanting a spinal implant according to the present invention are disclosed in, for example, U.S. Pat. Nos. 5,489,307 and 5,865,847. The entire disclosure of each of these patents is incorporated herein by reference.

A lordotic distraction plug 10 and implant 20 are shown in FIG. 1. The distraction plug 10 has a leading end 1, a trailing end 2 and a body 3. The diameter of the distraction plug 10 is stated by reference to the largest diameter 4 along the length "L" of body 3. The distraction plug 10 is cone shaped and has an included angle x of about 1° to 20°. The included angle x in the illustrated embodiment is about 8°. The length L of tapered plug 10 can vary. For this discussion, the length of tapered plug 10 is 26 mm, which is representative of the depth of the implant bore to be prepared for this example.

Implant 20 is also tapered and has an included angle x' which may be matched to correspond to the included angle of the distraction plug. The leading end 21 and trailing end 22 include a leading end face 23 and trailing end face 24, respectively.

In the illustrated system, when selecting the appropriate size distraction plug 10, and when the distraction plug 10 is inserted into the disc space through an anterior approach, the trailing end face 5 of distraction plug 10 is preferably placed approximately at the anterior margins of the adjacent vertebrae. Hence, because the final position of the distraction plug can provide the first reference point in this embodiment, positioning the trailing end face 5 at the anterior margin will cause the trailing end face 24 of implant 20 to be recessed posteriorly from the anterior margin of the vertebrae by the distance $D_1$ of distraction plug 10. In one preferred embodiment, $D_1$ is 4 mm, thus providing for the trailing end face 24 of implant 20 to be positioned about 4 mm posteriorly from the anterior face of the vertebrae. If the anterior margin of the vertebral bodies is rounded (in the transverse plane), the distraction plug 10 is preferably positioned further posterior (distal) to ensure that the trailing end face 24 of implant 20 will be totally contained within the margins of the vertebral bodies.

Figure 1A:
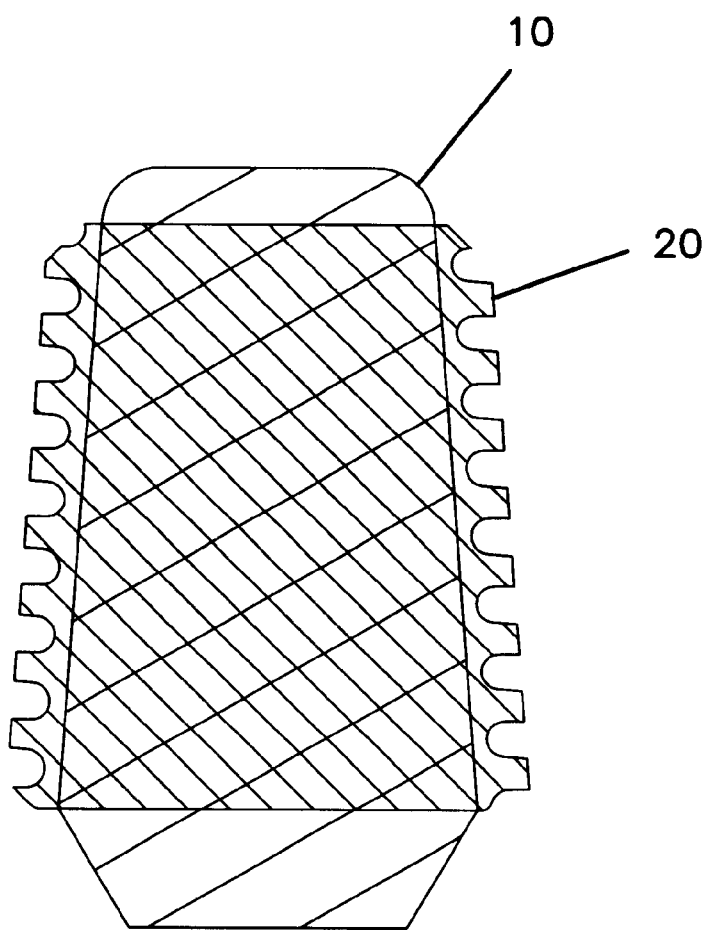
FIG. 1a illustrates a preferred relative arrangement of the distraction plug and implant when the implant has been positioned at the selected implant site.

According to the present embodiment, the position of distraction plug 10 within the disc space provides a first reference point for ensuring that implant 20 is positioned at the selected implant site. When using distraction plug 10 and implant 20 of FIG. 1, the implant 20 is preferably not advanced further posterior (distal) than the final placement of the distraction plug within the disc space. This relationship can be particularly critical to a lordotic system for ensuring the proper lordotic angulation, disc space height, annular tension and purchase of the interior surface of the implant into the vertebral endplates. FIG. 1a illustrates implant 20 overlying distraction plug 10 in a preferred relationship of selected implant position to final implant position.

Examples of problems associated with deviation of the final implant location from the selected implant position are described with reference to FIGS. 2–4. Each of FIGS. 2–4 represent a sagittal cross-section through adjacent lumbar vertebrae $L_A$ and $L_B$ with implant 20 located within intervertebral disc space IS. The letters "A" and "P" refer to the anterior (A) and posterior (P) aspects of vertebrae $L_A$ and $L_B$.

Figure 2A:
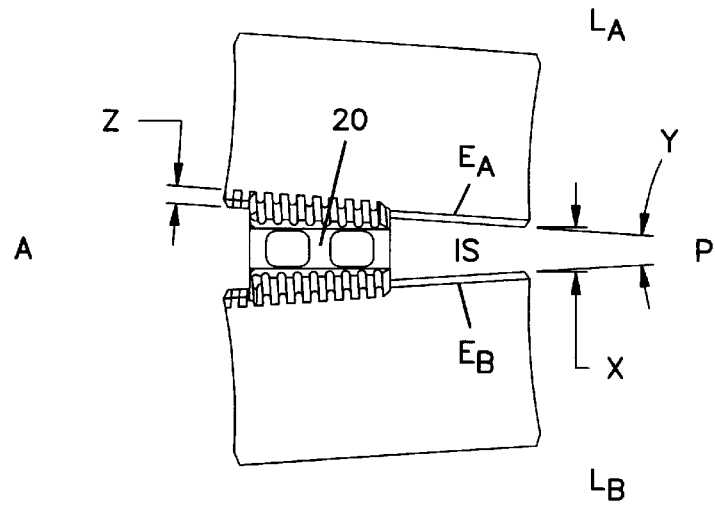
FIGS. 2a–c are sagittal cross-section views of adjacent lumbar vertebrae illustrating the effect on the intervertebral disc space height when the implant is positioned at, and outside, the selected implant site.
Figure 2B:
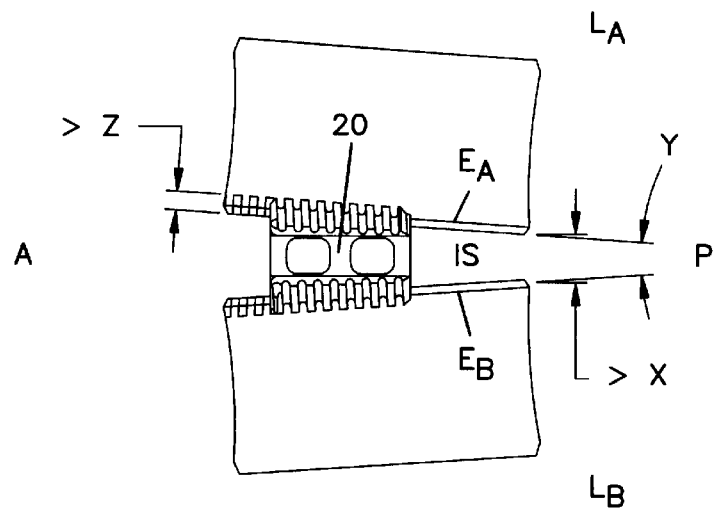
Figure 2C:
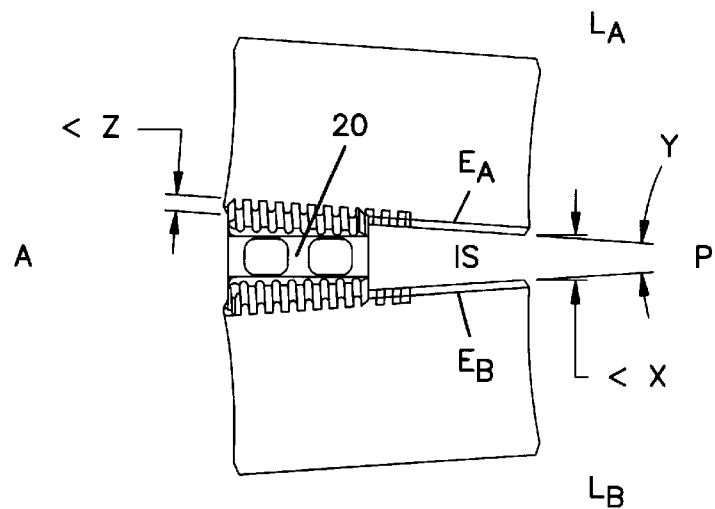

In FIG. 2a, implant 20 is appropriately positioned within the implant site at the selected implant position. In this position, implant 20 provides a disc space height "x," a lordotic angle "y" and an endplate ($E_A$ and $E_B$) purchase depth of "z." FIG. 2b illustrates a situation wherein implant 20 is positioned posterior to the selected implant position. In this situation, the disc space height between opposing end plates $E_A$ and $E_B$ is greater than x. In FIG. 2c, implant 20 is positioned anterior to the selected implant position causing the disc space height to be less than x.

Figure 3A:
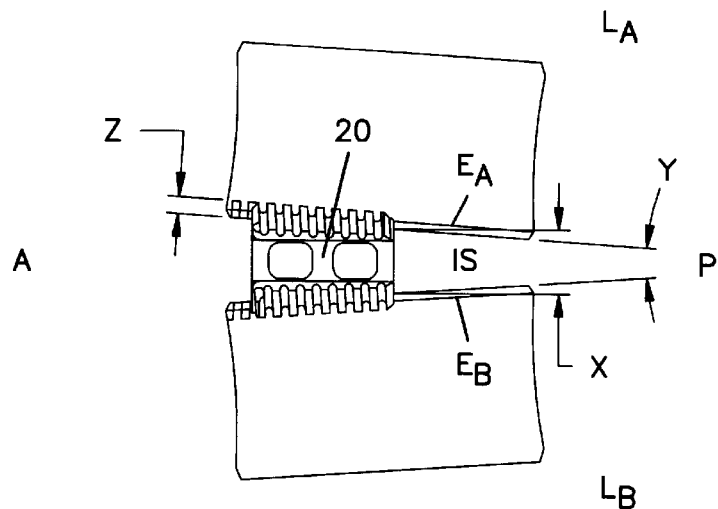
FIGS. 3a–c are sagittal cross-section views of adjacent lumbar vertebrae illustrating the effect on the lordotic angle between adjacent vertebrae when the implant is positioned at, and outside, the selected implant site.
Figure 3B:
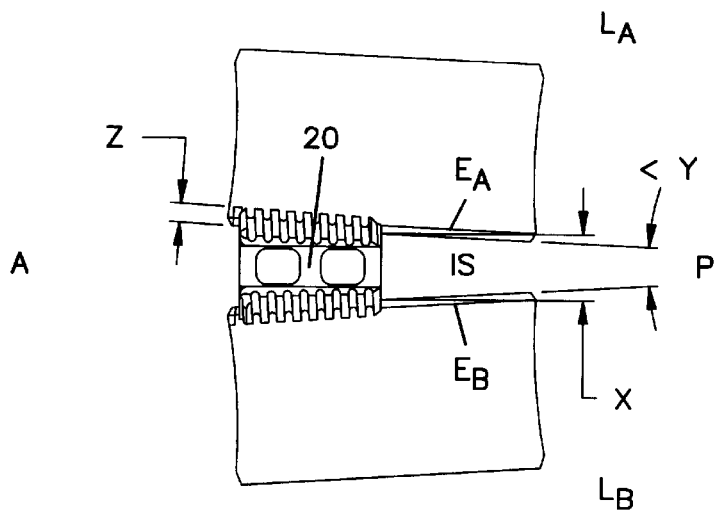
Figure 3C:
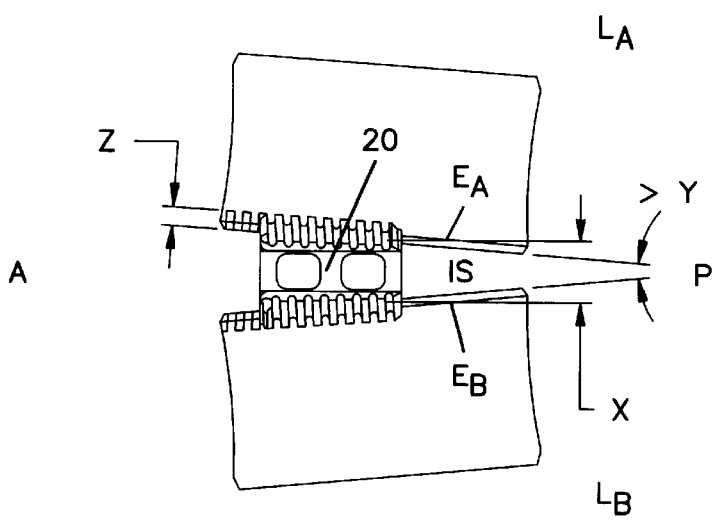

Referring to FIGS. 3a–3c, in FIG. 3a, implant 20 is positioned at the selected implant location. In FIG. 3b, implant 20 is positioned anterior to the selected implant position causing the lordotic angle to be less than y. In FIG. 3c, implant 20 is positioned posterior to the selected implant position causing the lordotic angle to be greater than y.

Figure 4A:
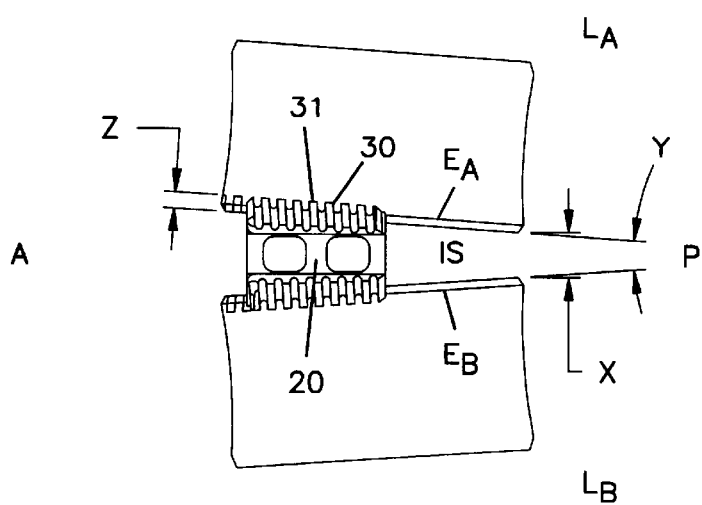
FIGS. 4a–c are sagittal cross-section views of adjacent lumbar vertebrae illustrating the effect on the purchase depth of an anchoring arrangement on the exterior surface of the implant into the end plates when the implant is positioned at, and outside, the selected implant site.
Figure 4B:
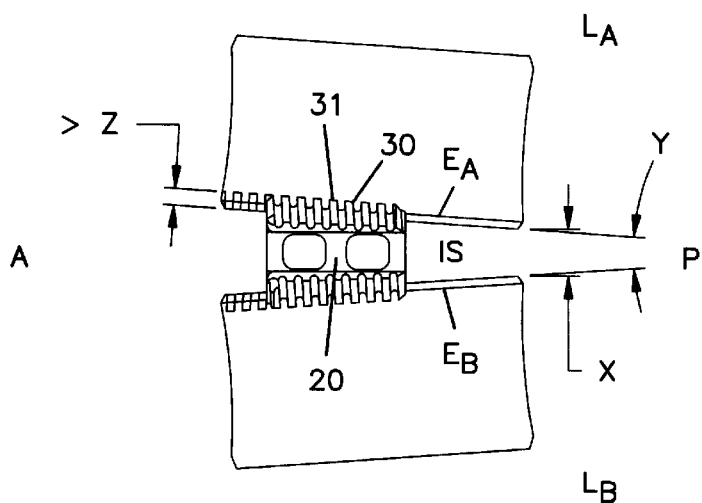
Figure 4C:
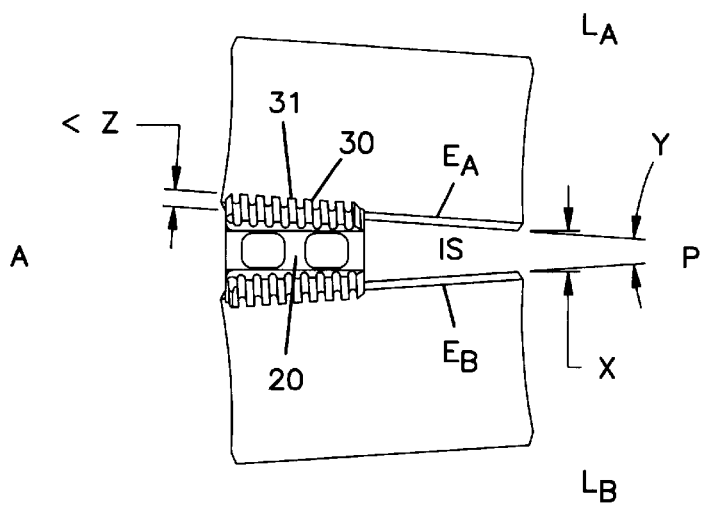

FIGS. 4a–4c illustrate the effect of improper implant positioning on the purchase of the anchoring arrangement 30 of the exterior surface of the implant into end plates $E_A$ and $E_B$. In the illustrations, anchoring arrangement 30 includes helical threads 31. However, as discussed previously, other anchoring arrangements (e.g., knurls, spikes, ridges, etc.) can be provided on the exterior surface of the implant to provide purchase into the endplates.

In FIG. 4a, implant 20 is positioned at the selected implant location and the purchase depth of thread 31 is z. In FIG. 4b, implant 20 is positioned posterior to the selected implant position causing the depth of purchase of threads 31 to be greater than z. In this situation, the purchase of implant threads 31 exceeds the thickness of the cortical bone at the end plates $E_A$ and $E_B$ and enter into the deeper cancellous bone. This can increase the chance of post-operative subsidence of the implant. In FIG. 4c, implant 20 is positioned posterior to the selected implant location causing the depth of purchase of threads 31 to be less than z.

It will be appreciated that while FIGS. 2–4 each illustrate a distinct event caused by improper implant positioning, one or more of the events described, or other event, can occur simultaneously in any particular situation. In addition, a particular disadvantage when performing a bilateral implantation using lordotic implants is that positioning the second implant too far posterior of the selected site after implantation of the first implant can cause loosening of the first implant.

To correct the position of implant 20 if the implant 20 is positioned anterior to the selected position, the surgeon must remove the implant and repeat the steps for preparing the implant site (e.g., reboring and retapping). To correct the position of implant 20 if the implant 20 is positioned posterior to the selected position, the surgeon must remove the implant and repeat the steps for preparing the implant site. However, in this situation, it is also likely that a larger diameter implant will be needed, thus requiring removal of a greater amount of cortical bone. The present invention reduces the need for repeating the procedure for preparing the implant site.

Having described a few problems which can occur when the final implant site deviates from the selected site, an embodiment of the present invention, which reduces the likelihood of occurrence of such problems, will now be described. Many instruments and methods suitable for use with this embodiment are fully described in U.S. Pat. Nos. 5,489,307 and 5,865,857, both patents having been previously incorporated herein by reference.

A. Radiographic Templating

Radiographic templates for plain x-rays or MRI or CT scans can be used to determine the proper size distraction plug required to restore an affected disc space to a desired height. The appropriate amount of distraction can be determined (e.g., appropriate size distraction plug) from radiographs and an appropriate size implant 20 is selected. Referring to FIG. 1, the diameter of the implant 20 is stated by reference to the minor diameter $D_M$ of external thread 25 at the greatest diameter 27 ($D_M$)of implant 20. Preferably, the diameter of the implant is at least 3 mm larger than the greatest diameter 4 of distraction plug 10 to achieve an optimal purchase of the implant thread 25 into the vertebral end plates.

Once the size and position of implant 20 is determined from the template, the appropriate implant length is selected. Preferably, the length of the implant is such that when implanted, the leading end 21 extends into the posterior one-third of the disc space.

B. Surgical Preparation, Positioning and Exposure

For the herein described anterior approach, the patient is placed into position and general anesthesia is administered. Known techniques for positioning are used. Typically, when performing a fusion procedure through an anterior approach, the patient is placed in supine position.

C. Alignment

Once the patient is prepared, the anterior aspect of the intervertebral disc space between the two vertebrae to be fused is exposed. The medial-lateral position for insertion of the implants can be determined using known procedures. In one preferred embodiment, the medial-lateral spacing is determined using an alignment guide such as the starter alignment guide assembly 36 illustrated in FIGS. 9 and 10 discussed in U.S. Pat. No. 5,489,307. Using the starter alignment guide, appropriate landmarks for implant placement can be created.

D. Discectomy

Disc material is then removed through the annulus. A drill can be inserted into each of the implant landmarks created in step C above through the annulus. Preferably, the drill is about 8 mm in diameter and is advanced into the disc space but does not extend beyond the posterior margin of the vertebrae. A pituitary rongeur or small curette can be inserted into the drill hole for removal of the nucleus material using known methods.

E. Vertebral Distraction and Annular Tension

Distraction plugs are then used to distract the vertebral bodies and tense the annulus prior to preparing the implant site. After ensuring that soft tissues, including nerves and vessels, are retracted from the implant site, a lordotic distraction plug having an 8° included angle and a diameter 24 corresponding to the implant size selected, as discussed above, is inserted into the disc space. The distraction plug is impacted into the intervertebral space until the anterior face 15 is approximately even with the anterior margin of the vertebral bodies. When the distraction plug is tight (secure) in this position, the proper distraction plug size has been reached. After the distraction plug has been inserted into the first side, the procedure is repeated on the opposite side.

The annular tension created by insertion of the distraction plug can be tested by attaching a handle to the distraction plug and pulling straight up on the handle attached to the distraction plug. If the distraction plug pulls out easily, distraction plugs having an increased diameter 4 are incrementally inserted from side to side until proper annular tension is reached. If the distraction plug must be advanced to a point where the anterior face 15 is deep to the anterior margin of the vertebrae to achieve appropriate tension, it may be advantageous to remove the plug and select a plug with a larger diameter 4. After the final placement of the distraction plug, the position of the distraction plug can be verified using appropriate methods including, for example, fluoroscopy or plain x-rays.

The implant length to be used is then selected as described above. The following chart lists the diameter $D_M$ size of implant to be used with the corresponding diameter 4 of the distraction plug selected.

TABLE 1

| Implant Size* | Distraction Plug Size Range |
|---|---|
| 15 mm | 11–12 mm |
| 17 mm | 13–14 mm |
| 19 mm | 15–16 mm |
| 21 mm | 17–18 mm |

*Implant Size is equivalent to the minor diameter of the thread at the large (anterior) diameter 27 of the implant.

F. Tooth Drill Tube Assembly

A hollow guide tube, such as drill tube 92 illustrated in FIG. 3 of U.S. Pat. No. 5,489,307 is selected having an inside diameter of a size sufficient to receive an implant having a $D_M$ of that selected in step E. In addition, while the present example is described using drill tube 92, a multi-lumen guide tube such as described in application U.S. Ser. Nos. 08/921,001, 09/116,747 can also be used.

Figure 5:
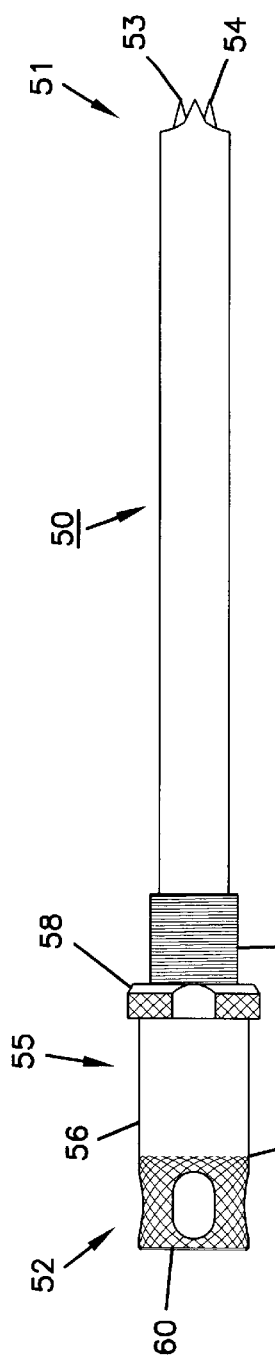
FIG. 5 is a side view one embodiment of a guide tube suitable for the invention.

Referring to FIG. 5, in one embodiment, hollow guide tube 50 includes distal end 51 and a proximal end 52. The distal end 51 includes an anchoring arrangement 53 comprising teeth 54. At the proximal end 52, guide tube 50 includes an affirmative stop arrangement 55 such as an adjustable affirmative stop arrangement 56. As illustrated, adjustable affirmative stop arrangement 56 includes threads 57, lock nut 58 and stopping member 59. The distance of the proximal surface 60 to any point at the distal end of guide tube 50 can be varied by threading stopping member 59 proximally or distally along threads 57. Once the appropriate position of proximal surface 60 is determined (discussed below), lock nut 58 is threaded to lock against stopping member 59 to prevent inadvertent movement. As discussed below, the proximal surface 60 sets the distance at which distal advancement of all instruments passed through guide tube 50 will be stopped.

Also, in some embodiments, distal end 51 can include diametrically opposed "paddles" for insertion into the disc space. Suitable paddles are known in the art. These paddles can provide for distraction of the vertebrae. In some embodiments, the paddles can have a lordotic taper to provide a selected degree of lordosis when inserted into the disc space. The position of the paddles within the disc space can be used to establish the first reference point.

G. Drill Tube Placement and Depth Adjustment

Figure 6:
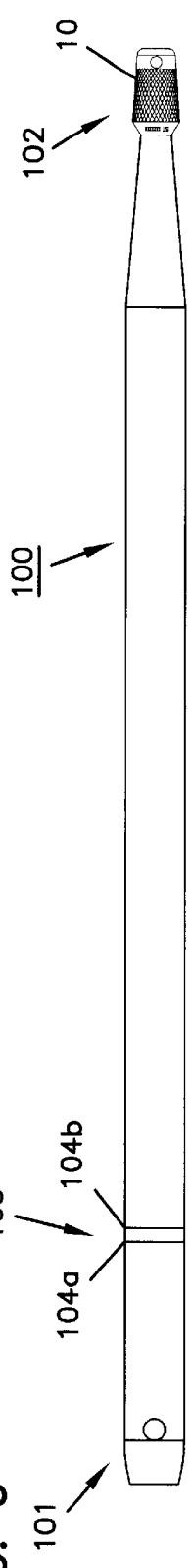
FIG. 6 is a side view of one embodiment of an obturator suitable for the invention.

Referring now to FIG. 6, obturator 100 includes a proximal end 101 and a distal end 102 having distal mounting arrangement (not visible) for mounting to distraction plug 10. The transverse cross section of obturator 100 can be any shape, e.g., square, oval, or, as illustrated, circular. In one embodiment, the distal mounting arrangement is a threaded male end as seen in similar devices disclosed in U.S. Pat. No. 5,489,307. The threaded male end can be received by a threaded bore at the proximal end of distraction plug 10. In an alternative embodiment, the distraction plug and obturator can be a single unit.

Near the proximal end 101, obturator 100 includes an indicator arrangement 103 such as laser etched marks 104a and 104b. In this embodiment, the indicator arrangement 103 can be a scribed line, machined groove, printed line, etc. Such indicator arrangements may partially or fully extend along the perimeter of the obturator.

After the distraction plug 10 is positioned as discussed in step E, the mounting arrangement at the distal end 102 of obturator 100 is mounted to the distraction plug 10 that is positioned on the side of the vertebrae at which the first implant bore will be prepared. After obturator 100 is mounted to distraction plug 10, guide tube 50 is passed over obturator 100 and the proximal end 52 of the guide tube 50 is urged distally, using known methods (e.g., hammer, mallet, etc.), until the teeth 54 are set into the surface of the vertebral bodies. Once the teeth 54 are set, the proximal surface 60 of affirmative stop arrangement 55 is aligned with the indicator arrangement 103, such as laser mark 104a. In the present embodiment, each of laser marks 104a and 104b correspond to a particular implant size (e.g., 104a can correspond to a 20 mm implant length and 104b to a 24 mm implant length). It will be appreciated that additional marks can be added for additional implant lengths. Once the proximal surface 60 of stop arrangement 55 is aligned with the appropriate mark (104a and 104b) of indicator arrangement 103 for the particular implant size, lock nut 58 is snugged against the affirmative stop arrangement 55 to fix the proximal surface 60 in a desired position.

Once the drill tube 50 is secure and alignment is verified, the obturator 100 and attached distraction plug 10 can be removed. In the present embodiment, the distraction plug 10 can typically be removed by rotating the obturator 100 clockwise and pulling proximally while applying downward or distal pressure to the guide tube 50.

H. Vertebral Reaming with Reamer

Figure 7:
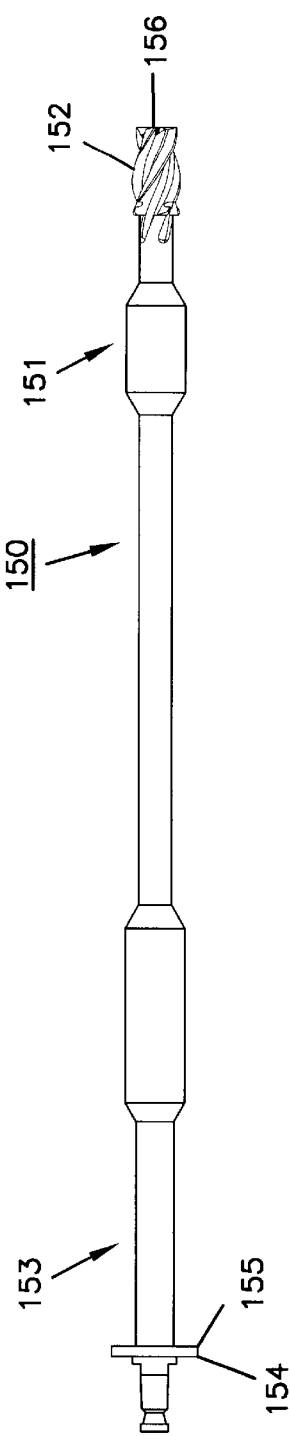
FIG. 7 is one embodiment of a reamer suitable for the invention.

Referring now to FIG. 7, reamer 150 includes a distal end 151 having a cutting end 152 for drilling the implant bore. At the proximal end 153, the reamer 150 includes a limiting arrangement 154 such as flange 155. After guide tube 50 is positioned, reamer 150 can be passed distally towards the disc space and the implant bore reamed until the limiting arrangement 154 is stopped by affirmative stop arrangement 55. If the flutes 156 at cutting end 152 become clogged prior to reaching the final reaming depth of the implant site, reamer 150 can be removed while rotating clockwise. After the material in the flute is removed, reaming can be continued.

I. Bone Tapping

Figure 8:
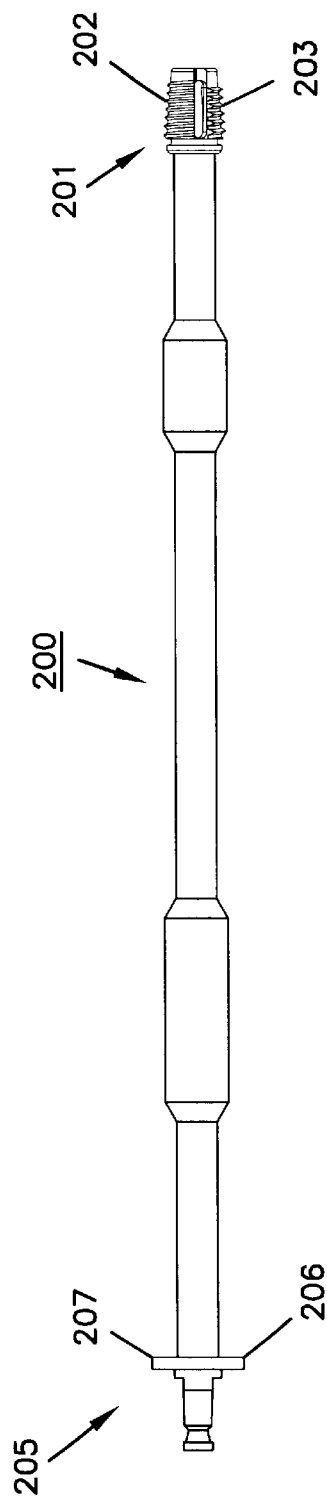
FIG. 8 is one embodiment of a tap suitable for the invention.

Referring to FIG. 8, bone tap 200 includes a distal end 201 having a tapping head 202 including threads 203. Tapping threads 203 can form female threads into the implant bore created by reamer 150. At the proximal end 205 of tap 200 is a limiting arrangement 206 such as flange 207 which prevents distal advancement of the tap beyond a point when flange 207 abuts against proximal surface 60 of affirmative stop arrangement 55.

J. Implanting the Implant

Figure 9:
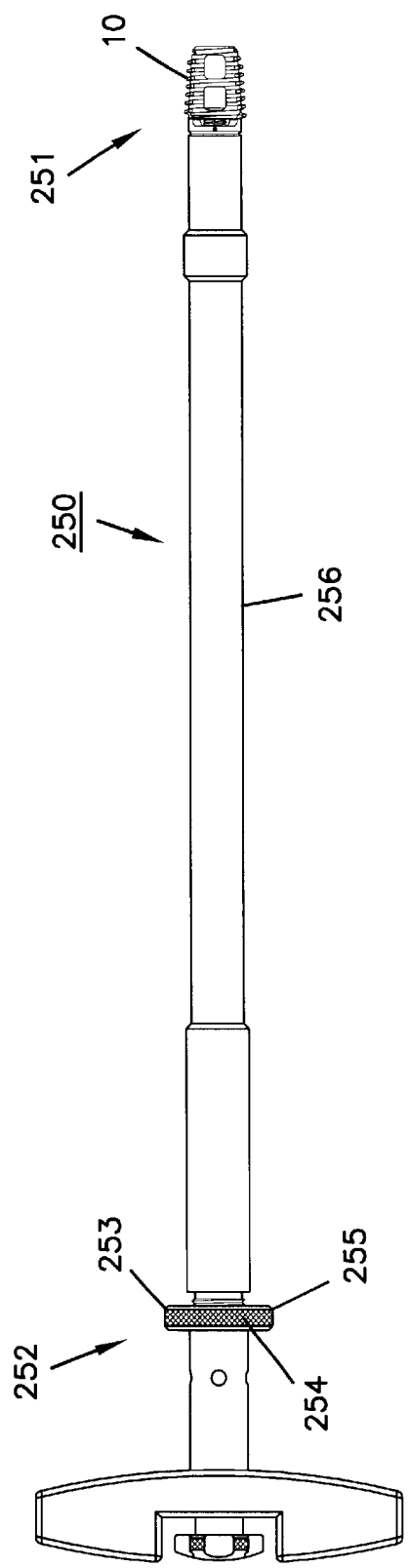
FIG. 9 is one embodiment of an implant driver suitable for the invention.

Referring now to FIG. 9, implant 20 can be mounted to the distal end 251 of implant driver 250. At the proximal end 252 implant driver 250 includes a limiting arrangement 253. In the illustrated embodiment, limiting arrangement 253 is an adjustable limiting arrangement 254. The adjustable feature can include a threaded locking ring 255 which can be threaded proximally or distally to accommodate a particular implant length.

In one embodiment, a single implant driver 250 can accommodate two different size implants. For example, distal advancement of locking ring 255 sets the limit for a first implant length and proximal retraction of locking ring 255 sets the limit for a second implant length. After the limiting arrangement 253 of the implant driver 250 is set to the appropriate implant length, the implant 20 can be positioned on the distal end 251 of the implant driver 250. The implant 20 can be packed with a bone graft or other osteoconductive, osteoinductive or similar material. While maintaining the alignment angle of guide tube 50 which was utilized during reaming and tapping, the implant/driver assembly is inserted into guide tube 50 and implant 20 is threaded into the implant bore. The proper placement of the implant can be verified radiographically by comparing to the pre-operative survey radiographs. The preferred relationship is shown in FIGS. 2a, 3a and 4a. After final positioning of implant 20, implant driver 250 can be removed.

Figure 10:
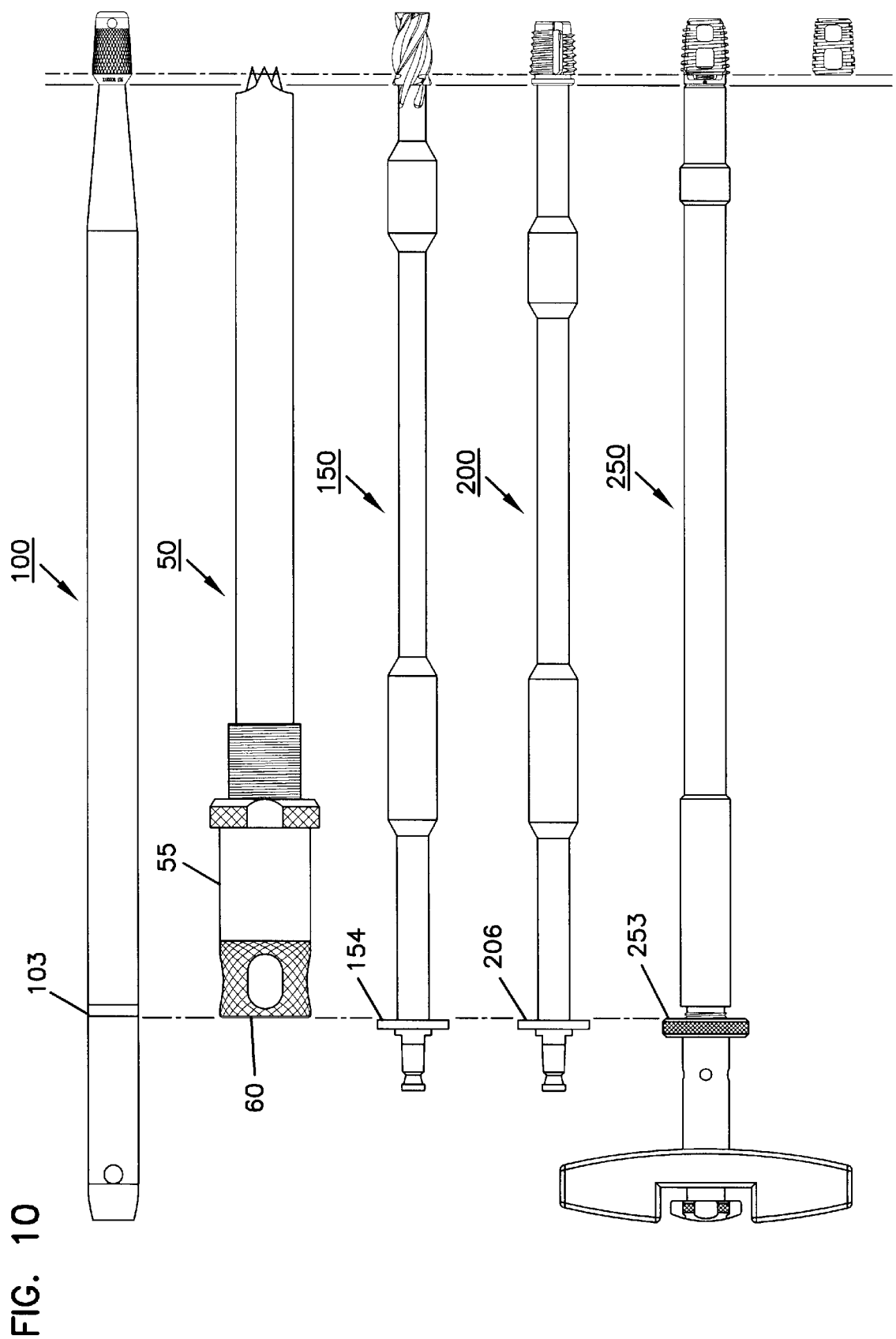
FIG. 10 illustrates the relative position of instruments when the proximal end of the instruments are affirmatively stopped based on a first reference point according to the principles of the invention.

FIG. 10 illustrates the relative alignment of the instruments described in the foregoing discussion of one embodiment of the invention. As illustrated in FIG. 10, once the proximal surface 60 of affirmative stopping arrangement 55 is aligned with indicator arrangement 103 of obturator 100, limiting arrangements 154, 206 and 253 of reamer 150, tap 200 and implant driver 250, respectively, provide for the distal advancement of the instruments only to the predetermined location. That location being determined by the first reference point, which in the present case is provided by distraction plug 10.

K. Placement of the Second Implant

After placement of the first implant, steps E–J are repeated for the second implant. If necessary, prior to removal of the second distraction plug, obturator 100 can be advanced distally to ensure that the second distraction plug is snug within the intervertebral disc space. The drill tube 50 can then be passed over obturator 100 and the procedure repeated.

L. Alternative Embodiments of Indicator Arrangements

Alternative embodiments of indicator arrangements will now be described with reference to FIGS. 11–16. Referring to the embodiment illustrated in FIGS. 11–12, the distal end 301 of obturator 300 includes a distal mounting arrangement 302 comprising a threaded male end 303 for mounting to distraction plug 10. At the proximal end 304, obturator 300 is configured to receive an obturator cap 305 which alone, or in conjunction with an indicator mark 306, such as mark 307, provides for positioning of the proximal surface 60 of affirmative stopping arrangement 55 of guide tube 50. Thus, according to this embodiment, rather than relying on visual alignment of the proximal surface 60 of affirmative stopping arrangement 55 with indicator mark 306, the proximal edge 308 of obturator cap 305 provides a stop for stopping the proximal movement of affirmative stopping arrangement 55 when proximal surface 60 of affirmative stopping arrangement 55 abuts against proximal edge 308 of obturator cap 305. Subsequently, locking nut 58 of guide tube 50 can be snugged against stopping member 59 to prevent inadvertent movement of proximal surface 60. FIG. 12 illustrates that obturator cap 305 axially slides on and off of the proximal end 304 of obturator 300.

FIG. 13 is a perspective view of an alternative embodiment of an obturator cap 320 having a C-shaped cross section. This embodiment provides for obturator cap 320 to laterally slide on and off the proximal end 304 of obturator 300. Either embodiment of an obturator cap (305, 320) can have different lengths, each length being sized for a particular implant length. These embodiments provide alignment of proximal surface 60 of affirmative stopping arrangement 55 without the need to rely on visual alignment.

FIGS. 14–16 illustrate an alternative indicator arrangement which eliminates the need for visual alignment of the proximal end of the guide tube. Referring to FIG. 14, obturator 400 includes a distal end 401 and a proximal end 402. A distraction plug 10 can be attached to the obturator using arrangements as previously described. For purposes of this discussion, the distal end of obturator 401 abuts with the proximal aspect of distraction plug 10 at junction 404. In this embodiment, indicator arrangement 403 includes a circumferential groove 405 in the shaft 406 of obturator 400. Groove 405 includes a proximal edge 407 and distal edge 408.

According to this embodiment, after distraction plug 10 and obturator 400 are positioned in the disc space, a guide tube, such as guide tube 50, is passed over the proximal end 402 of obturator 400. The proximal surface 60 of affirmative stopping arrangement 55 is aligned flush with edge 408 by stop ring 420. To do so, stop ring 420 is slid onto obturator 400 in the region of groove 405. As illustrated, rims 421 and 422 of stop ring 420 fit snugly within edges 407 and 408 of obturator 400. FIG. 15a is a sectional view through a—a of stop ring 420 of FIG. 15. FIG. 15b illustrates that when stop ring 420 is positioned over groove 405, a portion of rim 422 extends beyond the diameter of shaft 406 of obturator 400 to create a surface 425 against which proximal surface 60 can abut against to stop precisely at the level of edge 408.

Additional stop rings, such as stop ring 430 illustrated in FIG. 16, can also be used to align proximal surface 60 at predetermined locations, such as mark 411, for different length implants using obturator 400. FIG. 16a is a section view through a—a of FIG. 16. As illustrated in FIG. 16a, stop ring 430 includes rims 431 and 432 and shoulder 433. Rim 431 and shoulder 433 fit within edges 407 and 408 of groove 405. As best shown in FIGS. 16a and 16b, stop ring 430 includes an extended wall portion 434 which extends beyond shoulder 433. Extended wall portion 434 is of an appropriate length for stopping proximal surface 60 at mark 411. Different stop rings 430 can be made which have different length extended portions 434 for different length implants.

II. Implantation of an Implant Through Other Approaches

The principles, methods and instruments disclosed herein can be used for preparation of an implant bore and insertion of many types of fusion implants through an anterior, posterior or lateral approach.

Having disclosed the invention in a preferred embodiment, modifications and equivalents of the disclosed concepts may occur to one skilled in the art. It is intended that the scope of the present invention not be limited to the specific embodiment disclosed, but shall include such modifications and equivalents.

What is claimed is:

1. A method for preparing an implant site for implanting a spinal implant between adjacent vertebrae, the method comprising a step of:
    inserting a first end of a distraction plug into an intervertebral disc space between the adjacent vertebrae to position a second end of the distraction plug within the intervertebral disc space;
    attaching a first end of an obturator to the second end of the distraction plug, a second end of the obturator having an indicator arrangement at a predetermined distance from the first end of the obturator;
    positioning a distal end of a guide tube against an exterior surface of the vertebrae, the distal end of the guide tube positioned over the intervertebral disc space and in axial alignment with the distraction plug;
    aligning an adjustable affirmative stop of a proximal end of the guide tube relative to the indicator arrangement;
    removing the obturator and distraction plug;
    passing a first end of an instrument for preparing the implant site through the proximal end of the guide tube to the intervertebral disc space and advancing the first end of the instrument into the intervertebral disc space to prepare the implant site, advancement of the instrument being affirmatively stopped when a second end of the instrument contacts the proximal end of the guide tube.

2. The method according to claim 1 wherein the instrument is a reamer.

3. The method according to claim 1 wherein the instrument is a tap.

4. The method according to claim 1 wherein the indicator arrangement is a mark on the obturator.

5. The method according to claim 1 wherein the mark is laser etched.

6. The method according to claim 1 wherein the indicator arrangement is a groove.

7. The method according to claim 1 wherein the indicator arrangement includes a c-ring that cooperatively fits within a groove on the second end of the obturator.

8. The method according to claim 1 wherein the indicator arrangement is an obturator cap that mounts at the proximal end of the obturator.

9. The method according to claim 1 wherein the distal end of the guide tube includes paddles.

10. The method according to claim 1 wherein the distal end of the guide tube includes teeth for penetrating the exterior surface of the vertebrae.

11. The method according to claim 1 wherein the distraction plug is a lordotic distraction plug.

12. The method according to claim 1 wherein the implant site is prepared from an anterior aspect of the vertebrae.

13. The method according to claim 1, further comprising a step of adjusting the adjustable affirmative stop arrangement.

14. The method according to claim 1 wherein the proximal end of the guide tube comprises threads and the affirmative stop arrangement comprises a stopping member rotatably mounted to the proximal end of the guide tube and a lock nut rotatably mounted to the guide tube at a position distal to the stopping member.

15. The method according to claim 14, further comprising adjusting the adjustable affirmative stop arrangement by threading stopping member proximally or distally along the threads and threading the lock nut against the stopping member once the stopping member is in position.

16. A method for preparing an implant bore for implanting a spinal implant between adjacent vertebrae, the method comprising a step of:
    inserting a first end of a distraction device into an intervertebral disc space between the adjacent vertebrae to position a second end of the distraction device proximal to the intervertebral disc space, the second end of the distraction device having an indicator arrangement at a predetermined distance from the first end of the distraction device;
    positioning a distal end of a guide tube against an exterior surface of the vertebrae, the distal end of the guide tube positioned over the intervertebral disc space and in axial alignment with the distraction device;
    aligning an adjustable affirmative stop of a proximal end of the guide tube with the indicator arrangement at the second end of the distraction device;
    removing the distraction device;
    passing a first end of an instrument for preparing the implant bore through the proximal end of the guide tube to the intervertebral disc space and advancing the first end of the instrument into the intervertebral disc space to prepare the implant site, advancement of the instrument being affirmatively stopped when a second end of the instrument contacts the proximal end of the guide tube.

17. The method according to claim 16 wherein the distraction device comprises a distraction plug and an obturator.

18. The method according to claim 17 wherein the distraction plug and obturator are separable.

19. A kit for implantation of a spinal implant comprising:
    a distraction plug, the distraction plug having a leading end and a trailing end;
    a guide tube having a proximal end, a distal end and a lumen of sufficient size for passing the distraction plug therethrough;

an obturator, the obturator having a distal end for attaching to the trailing end of the distraction plug and a proximal end including an indicator arrangement, the indicator arrangement providing for alignment of the proximal end of the guide tube at a predetermined distance from the trailing end of the distraction plug;

a guide tube comprising a proximal end having an adjustable affirmative stop arrangement.

20. The kit according to claim 19 wherein the indicator arrangement is a mark on the obturator.

21. The kit according to claim 19 wherein the indicator arrangement includes stop ring that cooperatively fits within a groove on the proximal end of the obturator.

22. The kit according to claim 19 wherein the indicator arrangement is an obturator cap that mounts at the proximal end of the obturator.

23. The kit according to claim 19 wherein the adjustable affirmative stop arrangement comprises a plurality of threads, a lock nut, and a stopping member.

* * * * *